United States Patent
Lovette et al.

(10) Patent No.: US 6,407,813 B1
(45) Date of Patent: Jun. 18, 2002

(54) MEASUREMENT SYSTEMS AND METHODS FOR DETERMINING COMPONENT PARTICLE CONCENTRATIONS IN A LIQUID

(75) Inventors: Spencer M. Lovette, Katonah, NY (US); Norman C. Ford, Amherst, MA (US)

(73) Assignee: On-Line Instrumentation, Inc., Poughkeepsie, NY (US)

( * ) Notice: Subject to any disclaimer, the term of this patent is extended or adjusted under 35 U.S.C. 154(b) by 0 days.

(21) Appl. No.: 09/507,027

(22) Filed: Feb. 18, 2000

Related U.S. Application Data (60) Provisional application No. 60/120,858, filed on Feb. 19, 1999, and provisional application No. 60/120,857, filed on Feb. 19, 1999.

(51) Int. Cl.$^7$ .............................................. G01N 21/00
(52) U.S. Cl. ...................................... 356/338; 356/343
(58) Field of Search ................................. 356/337, 338, 356/340, 341, 343

(56) References Cited

U.S. PATENT DOCUMENTS

| | | | |
|---|---|---|---|
| 3,624,835 A | 11/1971 | Wyatt | |
| 3,869,209 A | * 3/1975 | Sigrist | ........................ 356/103 |
| 3,901,602 A | 8/1975 | Gravatt, Jr. | |

(List continued on next page.)

OTHER PUBLICATIONS

Srilaorkul et al, "Effect of Ultrafiltration of Skim Milk on Casein Micelle Size Dist. In Retentate", J. of Diary Sci., vol. 74, No. 1, 1991, pp. 50–57.
Parker et al, "Light Scattering Investigation of the Stability of Bovine Casein Micelles to Dilution", J. of Diary Research, No. 47, (1980), pp. 343–350.
Horne, David S., "Particle Size Meas. In Concentrated Latex Susp. Using Fibre–Optic Photon Correlation Spectroscopy", J. Phys. D: Appl. Phys. 22 (1989) pp. 1257–1265.
Horne, David S., "Dynamic Light Scattering from Casein Micellle Suspensions", Laser Light Scattering, Dec. 20, 1990, p. 489.
Munyua et al, "The Influence of Ca2+ on the Size and Light Scattering Properties of Casein Miclelles 1. Ca2+ Removal", Milchwissenschaft 35 (10) 1980, pp. 604–606.
Vreeman et al, "The Structure of Casein Micelles Between pH5.5 and 6.7 as Determined by Light–Scattering, Electron Microscopy & vol. Exp.", J. Diary Res. (1989) 56, pp. 463–470ec.

(List continued on next page.)

Primary Examiner—Frank G. Font
Assistant Examiner—Michael P. Stafira
(74) Attorney, Agent, or Firm—Wolf, Greenfield & Sacks, P.C.

(57) ABSTRACT

Methods and apparatus are provided for measuring component concentration in a liquid containing relatively large particles and relatively small particles. The invention may be utilized for measuring fat and casein concentrations in a dairy product, but is not limited to such use. A polarized light beam is directed through a scattering cell having first and second windows and containing a sample of the liquid. A normal to an exterior surface of the second window of the scattering cell is at or near Brewster's angle with respect to the light beam to reduce or eliminate reflections. A first light detector, positioned at an angle of about 5° to about 45° with respect to the light beam, detects scattered light from a first component of the liquid, such as fat particles. A second light detector, positioned at an angle of about 130° to about 160° with respect to the light beam, detects scattered light from a second component of the liquid, such as casein particles. When the liquid is a dairy product, the detector signals are representative of fat and casein concentrations. Component concentrations of a dairy product may be measured without requiring the use of a chemical diluent.

16 Claims, 8 Drawing Sheets

U.S. PATENT DOCUMENTS

| | | | |
|---|---|---|---|
| 3,972,625 A | * 8/1976 | Takahasi et al. | ............ 356/181 |
| 4,265,538 A | 5/1981 | Wertheimer | |
| 4,541,719 A | 9/1985 | Wyatt | |
| 4,548,500 A | 10/1985 | Wyatt | |
| 4,616,927 A | 10/1986 | Phillips et al. | |
| 4,693,602 A | 9/1987 | Wyatt et al. | |
| 4,710,025 A | 12/1987 | Wyatt et al. | |
| 4,766,083 A | 8/1988 | Miyashita et al. | |
| 4,907,884 A | 3/1990 | Wyatt et al. | |
| D329,821 S | 9/1992 | Wyatt et al. | |
| 5,229,839 A | 7/1993 | Hayashi et al. | |
| 5,305,073 A | 4/1994 | Ford, Jr. | |
| 5,679,955 A | 10/1997 | Schmidt et al. | |
| 5,705,816 A | 1/1998 | Ronge et al. | |
| 5,747,807 A | 5/1998 | Atkinson et al. | |
| 6,067,157 A | 5/2000 | Altendorf | |

OTHER PUBLICATIONS

Vreeman et al, "Size Dist. & Avg. Size Parameters of Casein Micelles Determined by Electron Microscopy In Bovine Milk Between pH 5.5 & 6.7", J. of Diary Res. (1991) 58, pp. 299–312.

Horne, David S., "Dynamic Light Scattering Studies of Concentrated Casein Micelle Suspensions", Laser Light Scattering in Biochemistry, 15, pp. 225–239.

Holt et al, "Mesaurements of the Size of Bovine Casein Micelles by Means of Electron Microscopy & Light Scattering", J. of Colloid & Interference Sci., vol. 65, No. 3, Jul. 1978, pp. 555–565.

* cited by examiner

MEASUREMENT SYSTEMS AND METHODS FOR DETERMINING COMPONENT PARTICLE CONCENTRATIONS IN A LIQUID

CROSS-REFERENCE TO RELATED APPLICATIONS

This application claims priority based on provisional application Ser. Nos. 60/120,858 and 60/120,857, both filed Feb. 19, 1999.

FIELD OF THE INVENTION

This invention relates to measurement systems and methods and, more particularly, to measurement systems and methods for determining component particle concentrations in a liquid containing a mixture of relatively large particles and relatively small particles, utilizing light scattering techniques. The invention is particularly useful for determining fat and casein concentration in dairy products, but is not limited to such use.

BACKGROUND OF THE INVENTION

It is frequently desirable to determine particle concentration in a liquid. Such measurements may be utilized in process control, research, and the like. In some cases, the liquid may contain particles of one type having one size distribution. In other cases, the liquid may contain particles of two or more types, each having a characteristic size distribution. In the latter case, determining particle concentrations is difficult because of interaction between measurements. An example of a liquid having two types of particles with different size distributions is milk and other dairy products.

Raw milk prices are determined by the fat content of the milk. In most retail markets, dairy processors standardize milk to various levels of fat, e.g., 1%, 2% and 3.25% in the United States. Also in cheese production, quality and yield can be optimized by standardizing the ratio of casein to fat in the milk used to make the cheese. Consequently, there is a need for an effective means of measuring fat and casein concentrations in milk. Standardization requires a robust measurement suitable for operation on the dairy production floor for process control applications.

Several automated techniques have been developed for measuring fat concentration in milk. Currently, measurement of the optical turbidity of milk provides the most accurate and stable instrument-based fat measuring technique. Simple broadband light attenuation measuring detectors are used. The milk sample is homogenized and is diluted with a high pH diluent, such as sodium hydroxide, to dissolve calcium caseinate from the milk, so that it does not interfere with the fat measurement. There are no accepted simple instrumentation methods for measuring casein concentration in milk.

Light scattering is a known technique for characterizing particles in a liquid. In a light scattering system, a liquid containing particles is passed through a sample cell having windows. A light beam is directed through the liquid, and light scattered by the particles in the liquid is analyzed to determine die characteristics of the particles. In one prior art system, the liquid sample is surrounded by an array of detectors which collect laser light scattered by the sample at different angles. In another prior art system, laser light scattered by the sample at a predetermined angle passes through an annular aperture and is focused on a photomultiplier. A light scattering system for molecular characterization is disclosed in U.S. Pat. No. 5,305,073 issued Apr. 19, 1994 to Ford, Jr.

All of the known prior art light scattering systems have had one or more disadvantages, including an inability to measure the concentration of relatively small particles in the presence of relatively large particles. Accordingly, there is a need for improved measurement systems and methods for determining component particle concentrations in a liquid, such as fat and casein concentrations in a dairy product.

SUMMARY OF THE INVENTION

According to a first aspect of the invention, apparatus is provided for measuring component concentration in a dairy product. The apparatus comprises a light source for generating a polarized light beam having a direction of polarization, a scattering cell, positioned in the light beam, for receiving a sample of the dairy product, a first light detector positioned at a first angle in a range of about 5° to about 45° with respect to the light beam and a second light detector positioned at a second angle in a range of about 130° to about 160° with respect to the light beam. The scattering cell has a first window and a second window, wherein the second window is farther from the light source than the first window, wherein a normal to an exterior surface of the second window is at or near Brewster's angle with respect to the light beam and wherein the direction of polarization of the light beam is parallel to a plane defined by the light beam and the normal to the exterior surface of the second window. The first light detector detects scattered light from a first component of the dairy product having relatively large particle sizes and generates a first detector signal that is representative of concentration of the first component in the sample of the dairy product. The second light detector detects scattered light from a second component of the dairy product having a relatively small particle sizes and generates a second detector signal that is representative of concentration of the second component in the sample of the dairy product. The first component may comprise fat, and the second component may comprise casein.

In a preferred embodiment, the first angle is about 40° and the second angle is about 140°. Because of refraction effects in the first and second windows, the actual scattering angles differ from the laboratory angles which define the positions of the light detectors, as described below. The light source may comprise a laser and a polarizing device.

According to another aspect of the invention, apparatus is provided for measuring casein concentration in a dairy product. The apparatus comprises a light source for generating a polarized light beam having a direction of polarization, a scattering cell, positioned in the light beam, for receiving a sample of the dairy product, and a light detector. The scattering cell has a first window and a second window, wherein the second window is farther from the light source than the first window, wherein a normal to an exterior surface of the second window is at or near Brewster's angle with respect to the light beam and wherein the direction of polarization of the light beam is parallel to a plane defined by the light beam and the normal to the exterior surface of the second window. The light detector is positioned at an angle in a range of about 130° to about 160° with respect to the light beam for detecting scattered light from casein particles and generating a detector signal that is representative of casein concentration in the sample of the dairy product.

According to a further aspect of the invention, apparatus is provided for measuring fat concentration in a dairy product. The apparatus comprises a light source for generating a light beam, a scattering cell, positioned in the light beam, for receiving a sample of the dairy product, and a light detector positioned at an angle in a range of about 5° to about 45° with respect to the light beam, for detecting scattered light from fat in the dairy product and generating a detector signal that is representative of fat concentration in the sample of the dairy product.

According to yet another aspect of the invention, a method is provided for measuring component concentration in a dairy product. The method comprises the steps of generating a polarized light beam having a direction of polarization, placing a sample of the dairy product in a scattering cell that is positioned in the light beam, detecting scattered light from a first component of the dairy product at a first angle in a range of about 5° to about 45° with respect to the light beam and generating a first detector signal, and detecting scattered light from a second component of the dairy product at a second angle in a range of about 130° to about 160° with respect to the light beam and generating a second detector signal. The scattering cell has a first window and a second window, wherein the light beam is incident on the second window after passing through the sample of the dairy product, wherein a normal to an exterior surface of the second window is at or near Brewster's angle with respect to the light beam and wherein the direction of polarization of the light beam is parallel to a plane defined by the light beam and the normal to the exterior surface of the second window. The first detector signal is representative of concentration of the first component in the sample of the dairy product, and the second detector signal is representative of concentration of the second component in the sample of the dairy product.

According to a further aspect of the invention, apparatus is provided for measuring component concentration in a liquid containing relatively large particles and relatively small particles. The apparatus comprises a light source for generating a polarized light beam having a direction of polarization, a scattering cell, positioned in the light beam, for receiving a sample of the liquid, a first light detector positioned at a first angle in a range of about 5° to about 45° with respect to the light beam, and a second light detector positioned at a second angle in a range of about 130° to about 160° with respect to the light beam. The scattering cell has a first window and a second window, wherein the second window is farther from the light source than the first window, wherein a normal to an exterior surface of the second window is at or near Brewster's angle with respect to the light beam and wherein the direction of polarization of the light beam is parallel to a plane defined by the light beam and the normal to the exterior surface of the second window. The first light detector detects scattered light from a first component of the liquid having relatively large particle sizes and generates a first detector signal that is representative of concentration of the first component in the sample of the liquid. The second light detector detects scattered light from a second component of the liquid having relatively small particle sizes and generates a second detector signal that is representative of concentration of the second component in the sample of the liquid.

BRIEF DESCRIPTION OF THE DRAWINGS

For a better understanding of the present invention, reference is made to the accompanying drawings, which are incorporated herein by reference and in which.

DETAILED DESCRIPTION

A measurement system in accordance with the present invention exploits the way in which the physical properties of different components in a sample affect light scattered by the sample. For example, fat and casein in milk have different size distributions. Fat globule size distribution in raw bovine milk ranges from about 0.2 to 30 micrometers in diameter. After homogenization, the fat globule size is reduced so that most fat globules are under 3 micrometers in diameter, yielding a size distribution from about 0.2 to 3 micrometers. Casein occurs naturally in micellular form in the size range from 10 to 200 nanometers (0.01 to 0.2 micrometers) in diameter.

The intensity of scattered light is a function of particle size, light wavelength and polarization direction, scattering angle and sample concentration. The scattered intensity at a small angle is dependent almost entirely on the concentration of the large fat globules in the milk sample, and the scattered intensity at a large angle is dependent primarily on the concentration of the smaller casein micells.

Figure 1:
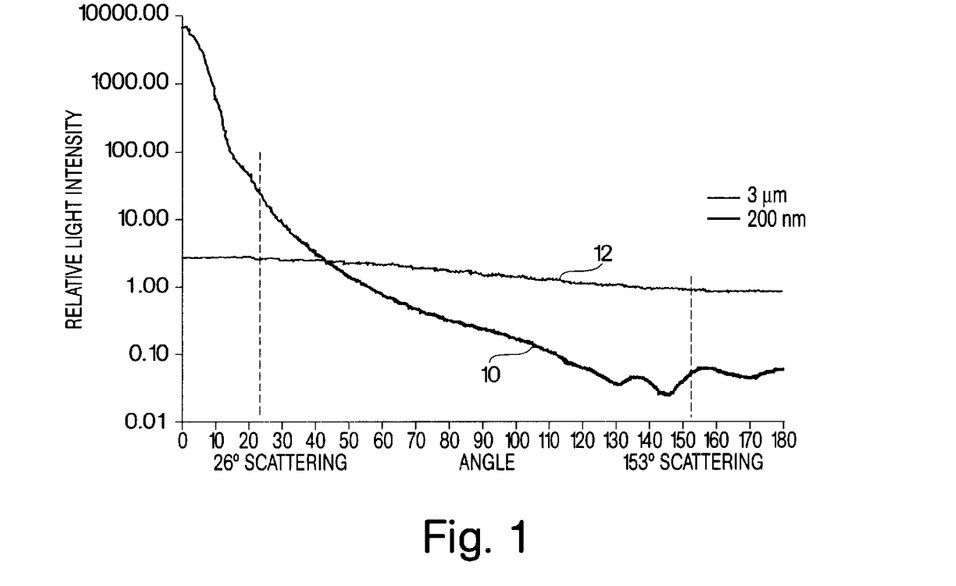
FIG. 1 is a graph of scattered light intensity as a function of scattering angle for relatively large particles and relatively small particles.

FIG. 1 shows the relative intensity of scattered light as a function of actual scattering angle for relatively large particles (3 micrometers) and relatively small particles (200 nanometers). Curve 10 represents the scattered light intensity from 3 micrometer particles, and curve 12 represents the scattered light intensity from 200 nanometer particles at a light wavelength of 800 nanometers. It may be observed that the relatively large particles exhibit a large variation, more than 100,000 to 1, in scattered light intensity as a function of scattering angle. By contrast, the relatively small particles exhibit a small variation, less than 10 to 1, in scattered light intensity as a function of scattering angle. For example, at an actual scattering angle of 26°, the intensity of light scattered from large fat particles substantially exceeds the intensity of light scattered from small casein particles. The reverse is true at an actual scattering angle of 153°. Thus, by separately measuring the scattered light at 40° and 140° as measured in the laboratory (actual scattering angles of 26.80° and 153.20°, respectively), the fat and casein concentrations in the milk can be determined without the use of a chemical diluent. The actual scattering angle differs from the scattering angle measured in the laboratory (laboratory scattering angle) because of refraction effects in the scattering cell windows.

Figure 2:
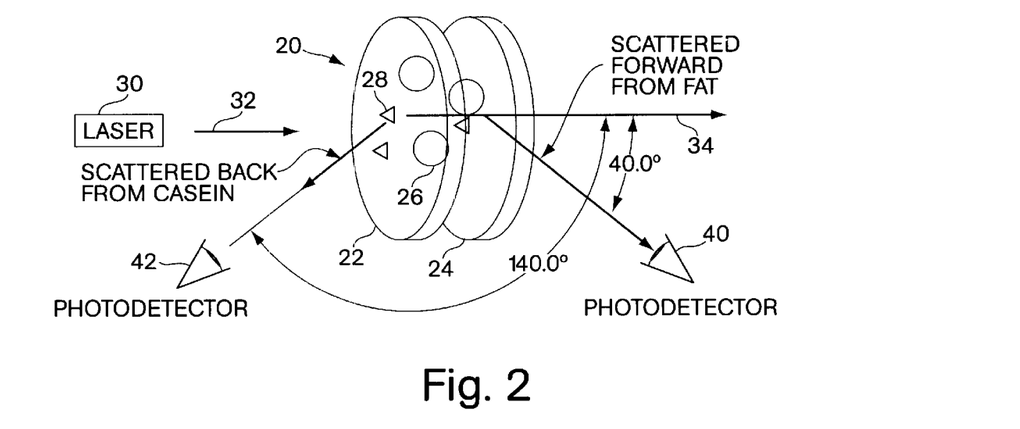
FIG. 2 is a simplified schematic representation of a measurement system in accordance with an embodiment of the invention.

A simplified schematic diagram of an embodiment of a measurement system in accordance with the invention is shown in FIG. 2. The measurement system is configured for measuring fat and casein concentrations in a dairy product. A scattering cell 20, represented in FIG. 2 by a first window 22 and a second window 24, contains a sample of a dairy product, such as diluted milk, for measurement. The dairy product contains fat particles 26 and casein particles 28. The sample is located between windows 22 and 24 and flows continuously through scattering cell 20. Scattering cell 20 is discussed in more detail below. A laser 30 directs a laser beam 32 along an optical axis 34 through scattering cell 20. Laser beam 32 has a direction of polarization perpendicular to the plane of FIG. 2. As described in detail below, windows 22 and 24 are oriented at Brewster's angle with respect to the polarized laser beam 32. The laser beam 32 passes through first window 22, through the sample, and through second window 24. As used herein, the "first" window refers to the scattering cell window that is closest to laser 30 or other light source, and the "second" window refers to the scattering cell window that is farthest from laser 30 or other light source. Thus, laser beam 32 is incident on the second window after passing through the liquid sample.

The laser beam 32 passing through scattering cell 20 is scattered by components of the dairy product sample. The angular distribution of the scattered light depends upon the properties of the particles in the sample, including their concentrations. In the embodiment of FIG. 2, a first photodetector 40 is located at an angle of 40° with respect to optical axis 32, and a second photodetector 42 is located at an angle of 140° with respect to optical axis 32. First photodetector 40 detects scattered light at an angle of 40° and provides a detector signal that is representative of fat concentration in the liquid sample. Second photodetector 42 detects scattered light at an angle of 140° and provides a detector signal that is representative of casein concentration in the liquid sample. As shown in FIG. 1, the scattered light intensity from fat is significantly greater than the scattered light intensity from casein at small angles, and the scattered light intensity from casein is significantly larger than the scattered light intensity from fat at large scattering angles. Accordingly, the measurement system of FIG. 2 provides measurements of the concentrations of fat and casein in the dairy product.

The separation between fat and casein measurements is incomplete. Thus, the detector signal from photodetector 40 at an angle of 40° contains a predominant component from fat and a lesser component from casein. Similarly, the detector signal from photodector 42 at an angle of 140° contains a predominant component from casein and a lesser component from fat. This is apparent from FIG. 1. The unprocessed detector signals therefore provide approximations to the fat and casein concentrations. As described below, more accurate values of fat and casein concentration can be obtained by processing the detector signals.

Figure 3:
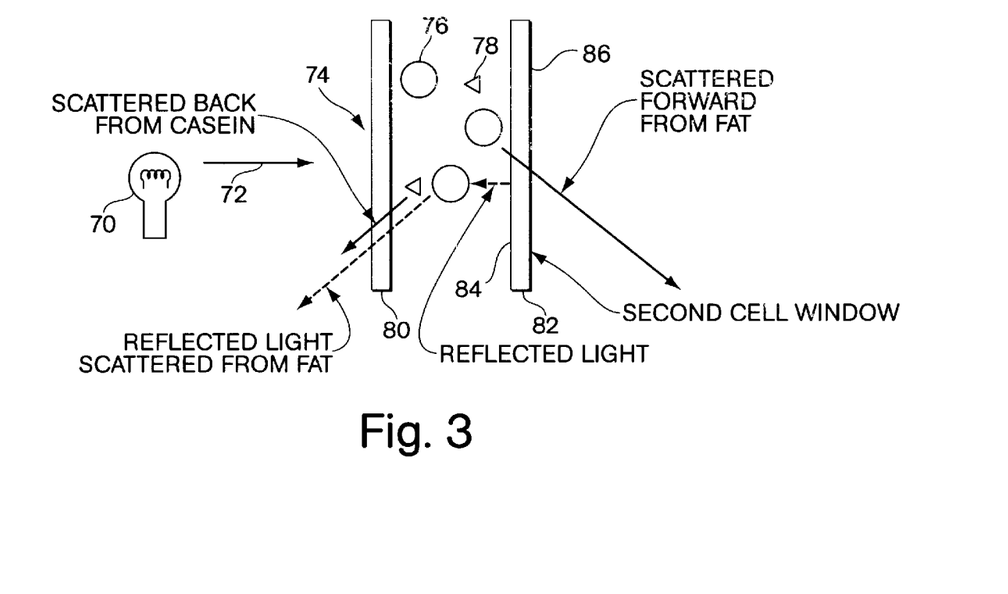
FIG. 3 is a schematic representation of a light scattering system, illustrating a difficulty in light scattering measurement of fat and casein in milk.

Generally, it is not possible to measure scattered light from small particles, such as casein, at large angles in the presence of large particles, such as fat, using prior art scattering cells. The reason is described with reference to FIG. 3, which is a schematic representation of a light scattering measurement system utilizing a conventional scattering cell. Light from a light source 70 is directed along an optical axis 72 through a scattering cell 74 containing a dairy product, including relatively large fat particles 76 and relatively small casein particles 78. A first window 80 and a second window 82 of scattering cell 74 have surfaces oriented perpendicular to optical axis 72. In the system of FIG. 3, the light beam from light source 70 is partially reflected by glass-liquid interface 84 and glass-air interface 86 of second window 82. The reflected light is scattered in a forward direction by fat particles 76 in the same direction as the light scattered by casein particles 78 in a backward direction from the main light beam. The reflected light scattered by fat particles 76 is more intense than the light scattered by casein particles 78 from the main light beam. For this reason, casein concentration cannot be measured in the system of FIG. 3.

Figure 4:
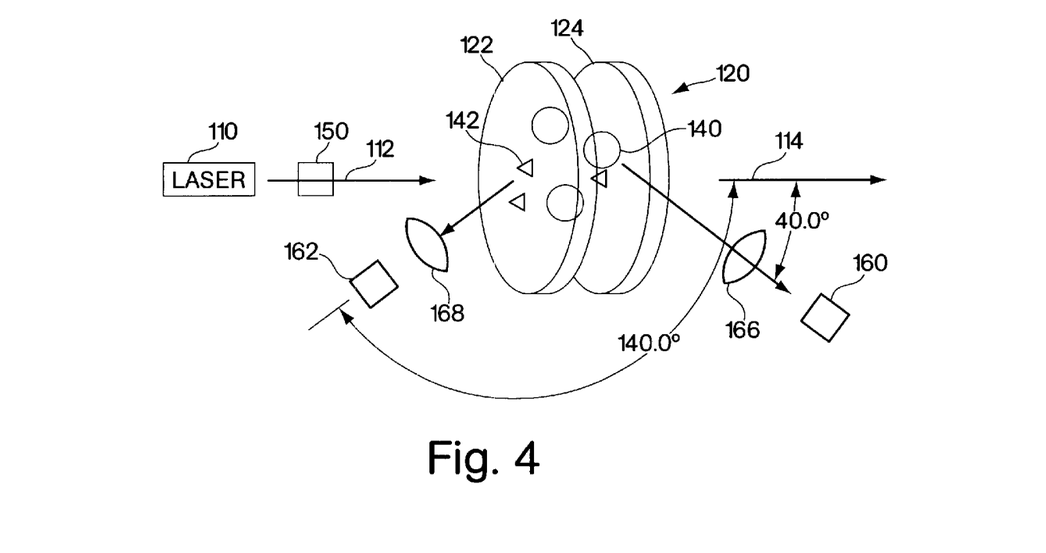
FIG. 4 is a top schematic view of an embodiment of a measurement system in accordance with the invention.
Figure 5A:
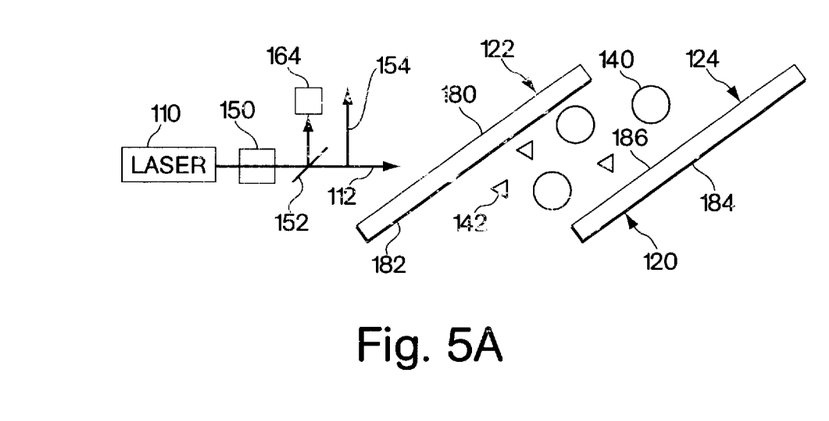
FIG. 5A is a partial side view of the measurement system of FIG. 4.
Figure 6:
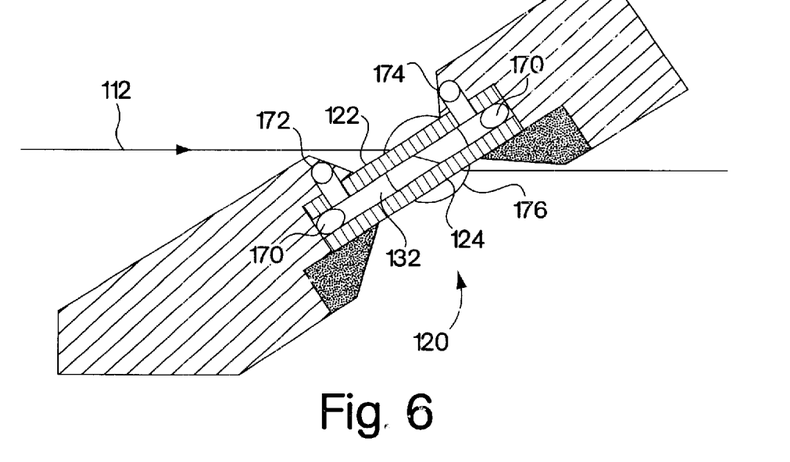
FIG. 6 is a cross-sectional side view of an implementation of a scattering cell utilized in the measurement system of FIGS. 4 and 5.

An embodiment of a light scattering measurement system in accordance with the invention is shown in FIGS. 4, 5A and 6. FIG. 4 is a schematic top view of the measurement system, and FIG. 5A is a schematic partial side view of the measurement system. FIG. 6 is a cross-sectional side view of an implementation of the scattering cell. Like elements in FIGS. 4, 5A and 6 have the same reference numerals. It will be understood that the orientation of the system can be changed and that the top and side designations are arbitrary.

A laser 110 directs a laser beam 112 along an optical axis 114 through a scattering cell 120. Scattering cell 120 includes a first window 122, a second window 124 and a housing 130 (FIG. 6). Housing 130 encloses a scattering cell volume 132 between first window 122 and second window 124. As indicated above, first window 122 is closest to laser 110 and second window 124 is farthest from laser 110. Scattering cell 120 contains a sample for measurement, including relatively large fat particles 140 and relatively small casein particles 142. As shown in FIG. 5A, laser beam 112 is directed through a polarizing device 150 and a beam splitter 152 before reaching scattering cell 120. As shown in FIG. 5A, polarizing device 150 causes laser beam 112 to have a vertical direction of polarization 154, so that a polarized light beam is incident on scattering cell 120. A first photodetector 160 is oriented at an angle of 40° in a horizontal plane with respect to laser beam 112. A second photodetector 162 is oriented at an angle of 140° in the horizontal plane with respect to laser beam 112. A third photodetector 164 is oriented at 90° with respect to laser beam 112 for monitoring the light intensity emanating from beam splitter 152. Photodetector 164 functions as a reference detector to normalize fluctuations in light intensity generated by laser 110.

Preferably, laser beam 112 is in a wavelength range from about 780 nanometers to about 1100 nanometers for measuring fat and casein concentrations in dairy products. In one example of the measurement system, laser 110 is a 780 nanometer, 2.5 milliwatt, polarized diode laser available from Melles-Griot. Although the laser provides a polarized laser beam, approximately 1% of the light has the wrong polarization and a separate polarizing device may be required.

Photodetectors 160, 162 and 164 maybe type S2386-8K available from Hamamatsu. Photodetectors 160 and 162 are not limited to angles of 40° and 140°, respectively, with respect to laser beam 112. More generally, photodetector 160 may be located at a laboratory angle in a range of about 5° to 45° for measuring scattered light from fat particles, and photodetector 162 maybe located at a laboratory angle in a range of about 130° to 160° for measuring scattered light from casein particles. As described above, photodetectors 160 and 162 do not provide complete separation between fat scattering measurements and casein scattering measurements. Lenses 166 and 168 form images of the scattering region on the active areas of photodetectors 160 and 162, respectively. The active areas of the preferred photodiodes are 5.8×5.8 millimeters.

As shown in FIG. 6, scattering cell 120 includes first window 122, second window 124 and housing 130, which enclose cell volume 132. The cell volume 132 thickness between first window 122 and second window 124 is defined by spacers 170. The liquid being measured flows through cell volume 132 from an inlet port 172 to an outlet port 174. According to a further feature, the scattering cell 120 may include a window, shown schematically at 176, positioned at 90° with respect to light beam 112, to permit measurement of 90° light scattering.

In one example of scattering cell 120, first window 122 and second window 124 each have a thickness of 0.15 inch and are fabricated of fused silica. Cell volume 132 is a circular disk having a diameter of 1.10 inch. The cell volume thickness between windows 122 and 124, defined by spacers 170, is 0.015 inch. Inlet port 172 and outlet port 174 have diameters of 0.10 inch. It will be understood that these scattering cell parameters and the system components identified above are given by way of example only and are not limiting as to the scope of the invention.

As indicated above, light scattered from relatively large particles at small angles is much more intense than light scattered at large angles. For example, a particle 3 micrometers in diameter scatters light about 1,000 times more intensely at an angle of 20° than at an angle of 160°. For this reason, it is not possible to make accurate measurements of small particles at large scattering angles using conventional light scattering cells when large particles are present. The reason is that, even if the surfaces of the cell windows have anti-reflection coatings, a small amount of the main light beam is reflected at the glass-air and glass-liquid interfaces. The light detected at a large scattering angle is made up of two components: (1) light scattered at the large angle from the incident light beam, and (2) light scattered at a small angle from the reflected beam parallel to the first component, as illustrated in FIG. 3. Even if the total reflected light intensity is only 0.5% (the reflection from a glass-water interface is about 0.3%), the undesired scattered light in the above example is five times as intense as the desired scattered light in a measurement at a scattering angle of 160°.

The reflected light may be eliminated or nearly eliminated by using a polarized light source and tilting at least the second scattering cell window, the window that is farthest from the light source, at or near Brewster's angle with respect to the polarized light beam. As known in the art, Brewster's angle is the angle between a light beam incident on an interface between two materials and a normal to the interface at which no reflection occurs. Brewster's angle, $\theta_B$, is defined as $\tan \theta_B = n_2/n_1$, where $n_1$ and $n_2$ are the indices of refraction of the materials on opposite sides of the interface, with $n_1$ corresponding to the medium through which the light beam is incident on the interface.

As illustrated in FIG. 5A, first window 122 has an exterior surface 180 and an interior surface 182; and second window 124 has an exterior surface 184 and an interior surface 186. In general, reflections from the surfaces 180 and 182 of first window 122 do not cause a problem, because the reflections do not pass through the liquid sample in scattering cell 120 and thus are not scattered toward photodetector 162. With respect to second window 124, light is reflected from interior surface 186 and exterior surface 184, when these surfaces are not oriented at Brewster's angle. Typically, the reflections from exterior surface 184 are more intense than the reflections from interior surface 186, because the indices of refraction at the glass-air interface (exterior surface 184) differ by more than the indices of refraction at the glass-liquid interface (interior surface 186).

In a first embodiment, the interior surface 186 and the exterior surface 184 of second window 124 are parallel, and window 124 is mounted at or near Brewster's angle with respect to light beam 112 for the glass-air interface of surface 184. The orientation of window 124 with respect to light beam 112 is illustrated in the schematic diagram of FIG. 5B. Light beam 112 is incident on surface 184 at Brewster's angle $\theta_B$ with respect to a normal 190 to exterior surface 184. Brewster's angle $\theta_B$ is determined as described above with respect to exterior surface 184, a glass-air interface. In this embodiment, second window 124 is preferably tilted at an angle $\theta_B$ of 55.463°, Brewster's angle for a fused silica-air interface. Second window 124 is further oriented such that the direction of polarization 154 of light beam 112 is parallel to a plane defined by light beam 112 and normal 190 to exterior surface 184 of second window 124. This configuration ensures little or no reflection of light beam 112 from exterior surface 184. For convenience, first window 122 may be mounted parallel to second window 124. However, first window 122 may have other orientations within die scope of the invention.

Figure 5B:
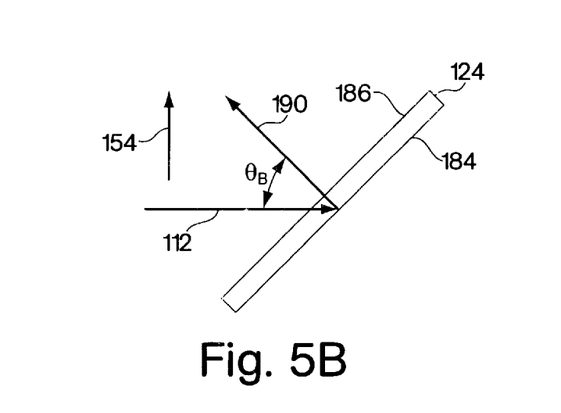
FIG. 5B is a schematic side view of a first embodiment of the second window of the scattering cell, illustrating the orientation of the second window with respect to the light beam.

Because exterior surface 184 is a glass-air interface and interior surface 186 is a glass-liquid interface, Brewster's angle is different for the two surfaces. Thus, when exterior surface 184 is oriented at or near Brewster's angle with respect to light beam 112, interior surface 186 is not oriented at Brewster's angle with respect to light beam 112, and a small fraction of light beam 112 may be reflected from interior surface 186. However, it has been found that the reflections from the glass-liquid interface of surface 186 are small and do not interfere to a significant degree with casein concentration measurements at a scattering angle of 140°.

Figure 5C:
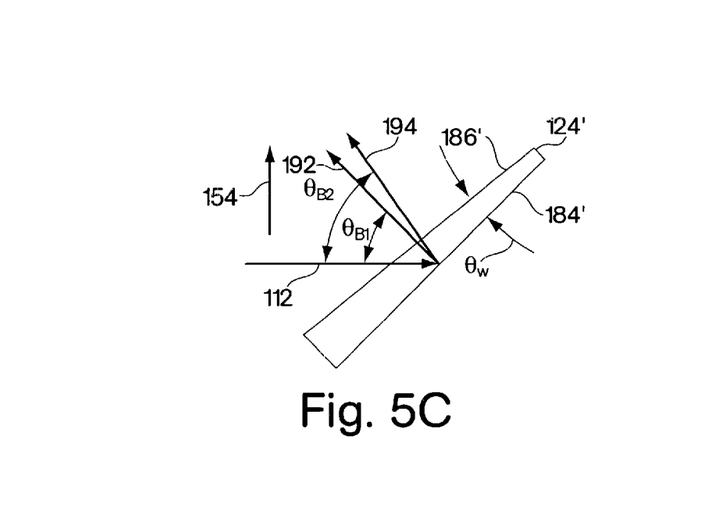
FIG. 5C is a schematic side view of a second embodiment of the second window of the scattering cell, illustrating the orientation of the second window with respect to the light beam.

In a second embodiment, both exterior surface 184 and interior surface 186 of second window 124 are oriented at or near Brewster's angle for the respective interfaces. As noted above, Brewster's angle is different for the interfaces at surfaces 184 and 186. In order to insure that each surface is oriented at the respective Brewster's angle, second window 124 is fabricated with a wedge shape. A wedge-shaped second window 124' is shown in FIG. 5C. Exterior surface 184' and interior surface 186' of second window 124' diverge at a wedge angle $\theta_W$ that is equal to the difference in Brewster's angle for the interfaces at surfaces 184' and 186'. In the example of a fused silica window with water as the fluid, the wedge angle $\theta_W$ is 7.997°. The wedge angle $\theta_W$ is exaggerated in FIG. 5C for illustrative purposes. Thus, second window 124' is oriented such that a normal 192 to exterior surface 184' is at or near Brewster's angle $\theta_{B1}$ with respect to light beam 112 for exterior surface 184', and a normal 194 to interior surface 186' is at or near Brewster's angle $\theta_{B2}$ with respect to light beam 112 for interior surface 186'. As in the first embodiment, the direction of polarization 154 of light beam 112 is parallel to a plane defined by light beam 112 and the normal 192 to exterior surface 184' of second window 124'. Using the wedge-shaped window 124' with both surfaces oriented at Brewster's angle, light beam 112 is not reflected from interior surface 186' or exterior surface 184'. In the second embodiment, first window 122 may be wedge-shaped for convenience of manufacturing or may have parallel surfaces. In general, it is not necessary to orient first window 122 at Brewster's angle. However, the use of two wedge-shaped windows may facilitate manufacturing of the scattering cell.

By tilting the windows of the sample cell 120 at or near Brewster's angle, as described above, little or no light is reflected back into the cell. The scattered light from the casein in the sample is measured at 140° without interference and is proportional to the casein concentration. A signal proportional to fat concentration is measured at 40°. Thus, referring again to FIG. 4, photodetector 160 provides a detector signal that is representative of fat concentration in the sample, and photodetector 162 provides a detector signal that is representative of casein concentration. As described above, photodetectors 160 and 162 do not provide complete separation between fat scattering measurements and casein scattering measurements.

Data analysis to determine fat and casein concentrations depends on the sample concentration. Sufficiently dilute samples generate single scattering (light rays scatter only once before exiting the cell) and produce a light intensity signal which increases linearly with component concentration. Fat and casein sample concentration are each related to measured light intensity at 40° and 140°, respectively, by $Y=mX+b$, where X is the measured light intensity, and m and b are calibration coefficients for the specific system.

More concentrated samples generate multiple scattering, wherein light rays scatter from more than one particle before exiting the cell. Component concentration is given by a polynomial equation in which the higher order terms account for multiply scattered light. Fat and casein concentrations may each be calculated from measured light intensity at 40° and 140°, respectively, by $Y=aX+bX^2+c$, where X is the measured light intensity, and a, b, and c are calibration coefficients for the specific system.

Since fat contributes to some of the scattered light measured at 140° due to both multiple and single scattering, and casein contributes to some of the scattered light measured at 40° for the same reasons, more accurate results may be calculated using polynomial expressions of multiple variables. For example, fat concentration may be calculated from $F=aX+bX^2+cZ+dZ^2+e$, where X is the light intensity measured at 40°, Z is the light intensity measured at 140°, and a, b, c, d, and e, are calibration coefficients for the specific system. Casein concentration may be calculated from $C=fX+gX^2+hZ+iZ^2+j$, where X is the light intensity measured at 40°, Z is the light intensity measured at 140°, and f, g, h, i and j are calibration coefficients for the specific system. Other mathematical forms which account for the non-linearity of specific implementations will yield optimum results for those implementations. The calibration coefficients may be determined experimentally for a particular system.

The calibration coefficients may be determined by the following steps.
1. Obtain two samples with known casein and fat concentrations, one with high fat concentration and low casein concentration, and the other with low fat concentration and high casein concentration.
2. Make a number of mixtures of the two samples to obtain second samples with a range of concentrations of fat and casein.
3. Make light scattering measurements on the second samples.
4. Use standard curve fining techniques to determine the calibration coefficients from the results of the scattering measurements.

Figure 9:
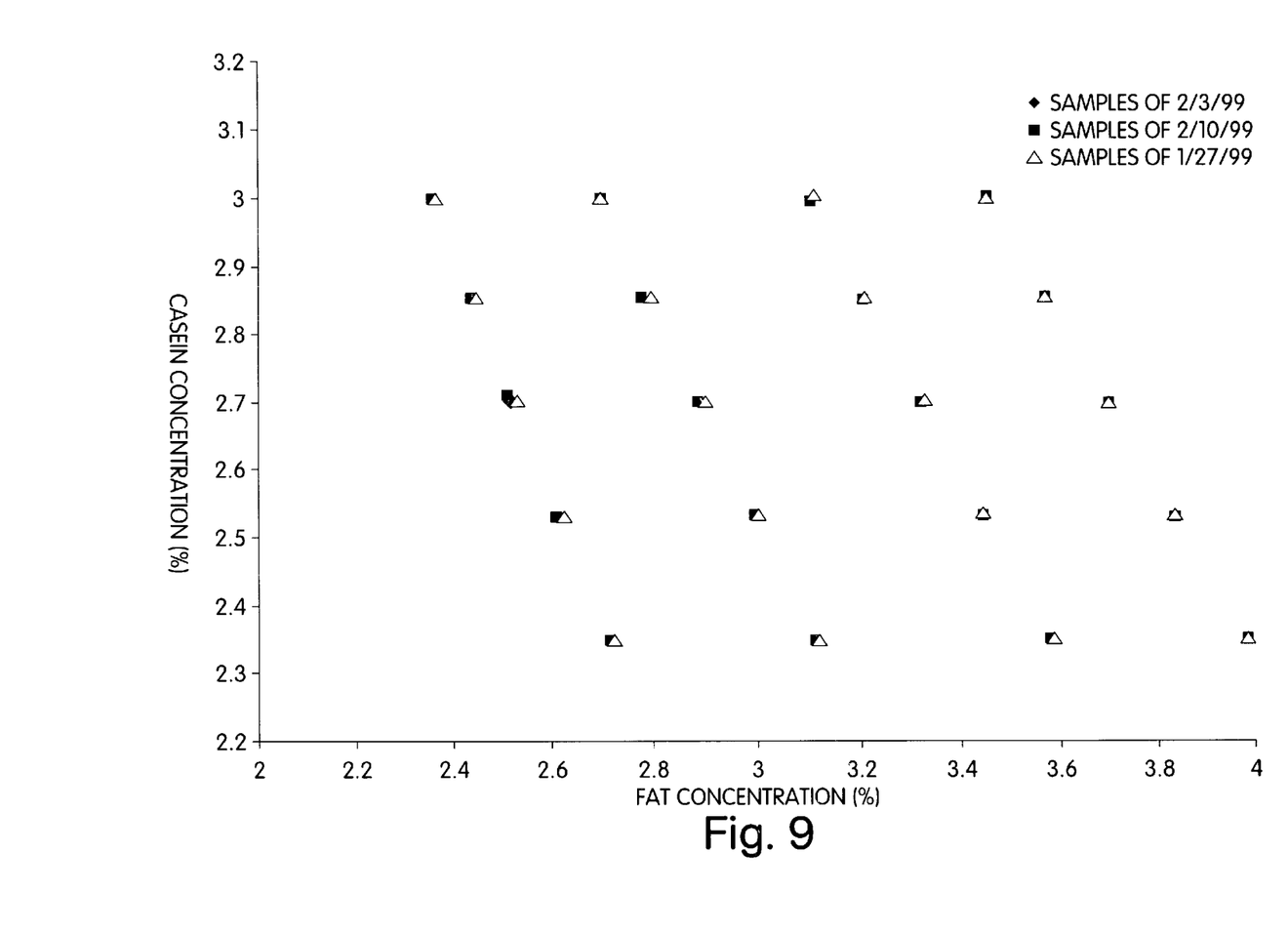
FIG. 9 is a graph of sample composition wherein casein concentration in percent is plotted on the vertical axis and fat concentration in percent is plotted on the horizontal axis.
Figure 10:
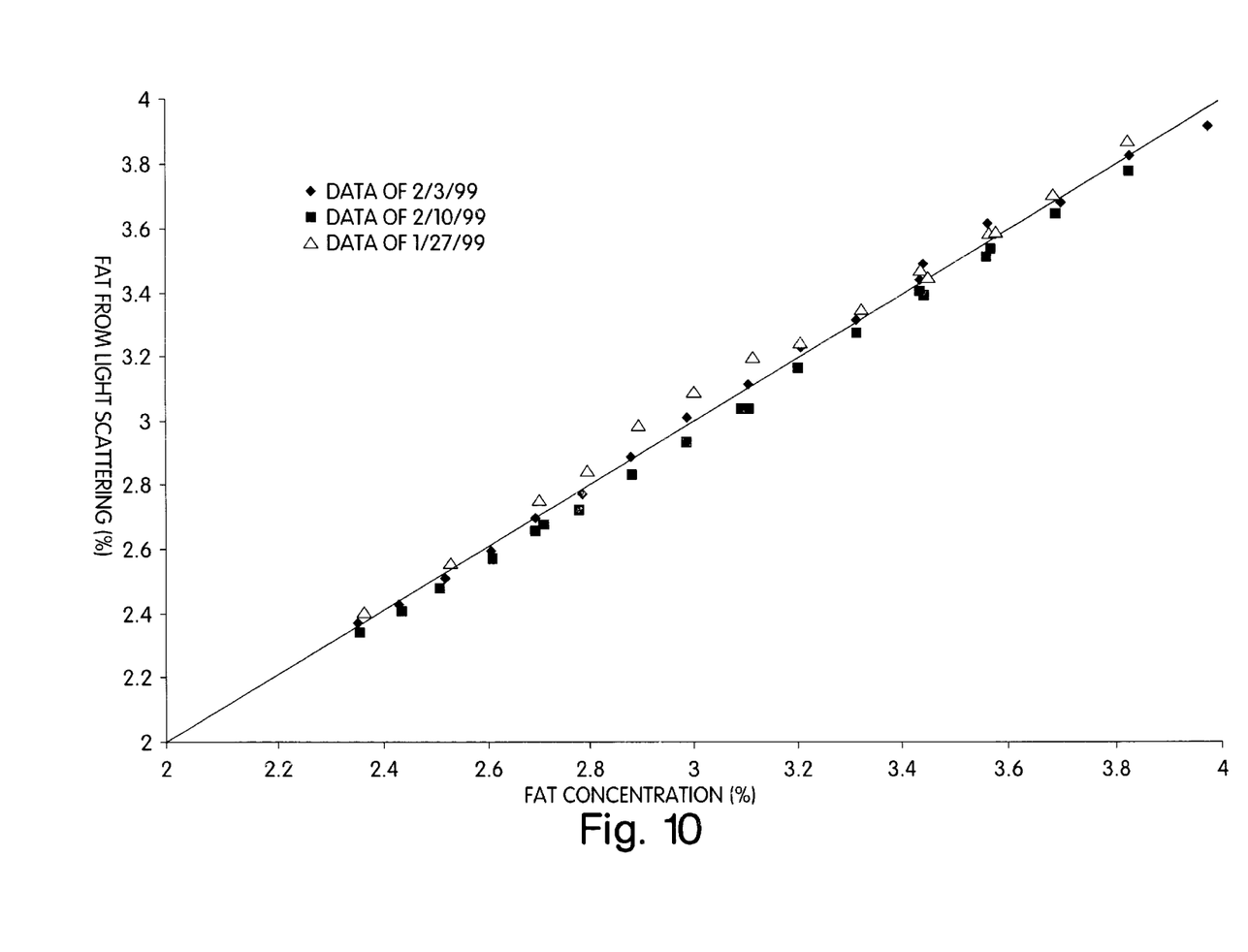
FIG. 10 is a graph that compares fat concentration in percent determined from light scattering measurements, plotted on the vertical axis, to fat concentration in percent determined from dilution, plotted on the horizontal axis.
Figure 11:
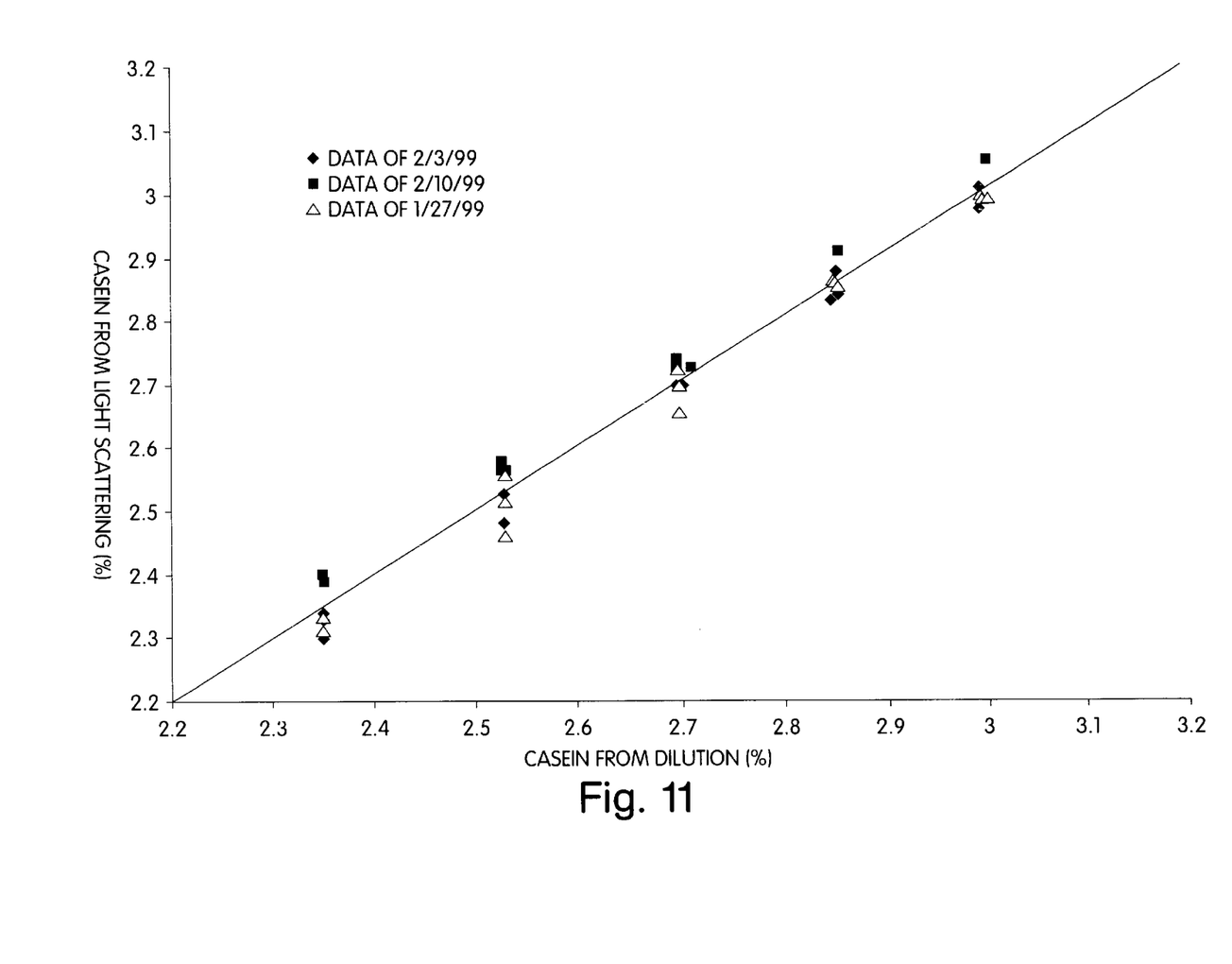
FIG. 11 is a graph that compares casein concentration in percent determined from light scattering measurement, plotted on the vertical axis, to casein concentration in percent determined from dilution, plotted on the horizontal axis.

This process is illustrated in FIGS. 9–11. FIG. 9 shows the casein and fat concentrations for twenty different samples. The casein concentration in percent is plotted on the vertical axis, and the fat concentration in percent is plotted on the horizontal axis. FIG. 10 shows the fat concentrations determined from light scattering measurements compared to fat concentrations determined from dilutions. In FIG. 10, fat concentration in percent determined from light scattering measurements is plotted on the vertical axis, and fat concentration in percent determined from dilution is plotted on the horizontal axis. FIG. 11 shows the casein concentrations determined from light scattering measurements compared to casein concentrations determined from dilutions. In FIG. 11, casein concentration in percent determined from light scattering measurements is plotted on the vertical axis, and casein concentration in percent determined from dilution is plotted on the horizontal axis.

Figure 7:
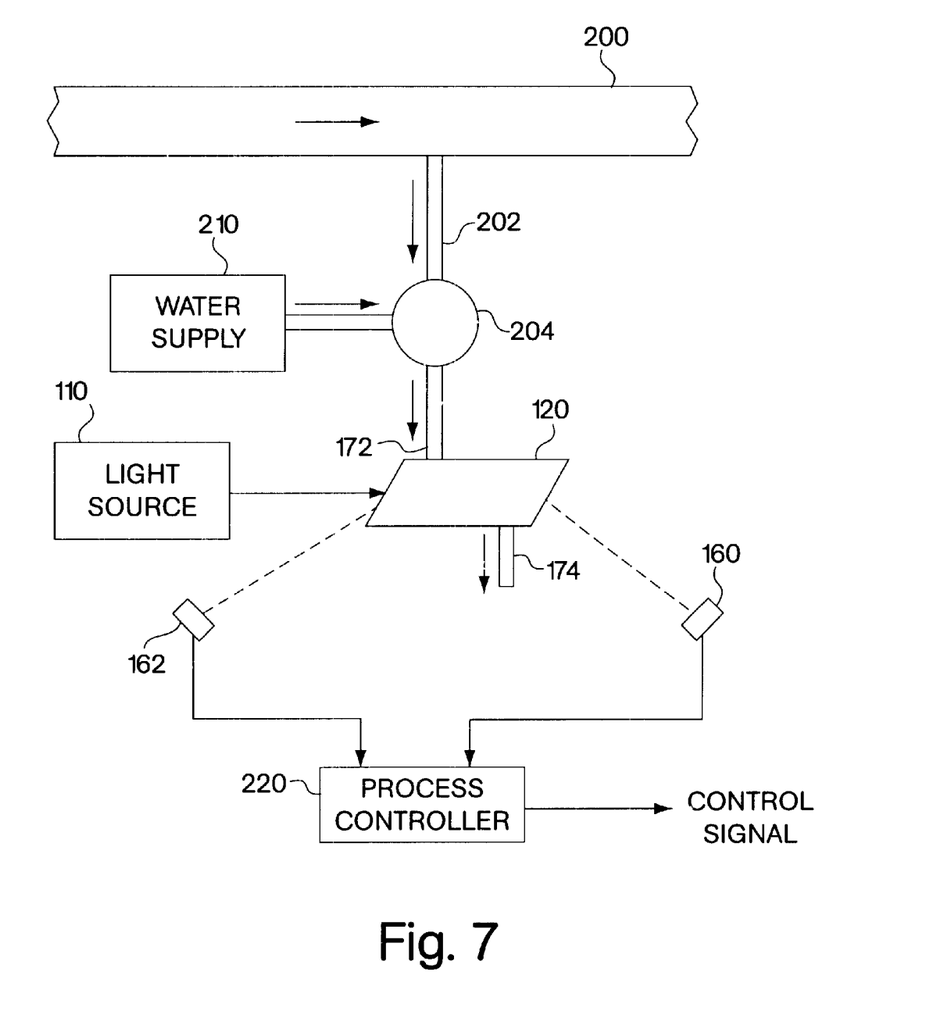
FIG. 7 is a block diagram that illustrates an application of the system for measuring component concentration in dairy products in accordance with the invention.

A simplified block diagram of an example of an application of the measurement system of the present invention in the dairy processing industry is shown in FIG. 7. FIG. 7 may represent a part of a cheese making facility. A system of the type shown in FIGS. 4–6 and described above is utilized. Like elements in FIGS. 4–7 have die same reference numerals. A conduit 200 carries a dairy product, such as milk, for use in the process. A sample of the dairy product is diverted through a smaller conduit 202 to a first inlet of a mixing valve 204. A water supply 210 provides water to a second inlet of mixing valve 204. Mixing valve 204 provides the ability to dilute the dairy product with water to facilitate light scattering measurements. In a preferred embodiment, milk is diluted with eight parts water to one part milk to provide a suitable sample for light scattering measurements. However, it will be understood that different dilution ratios may be utilized within the scope of the invention.

The diluted milk is provided as a liquid sample through inlet port 172 of scattering cell 120. The liquid sample passes through scattering cell 120 and outlet port 174 and is discarded after measurement. Light scattering measurements of fat concentration are made by photodetector 160 at a scattering angle of 40°, and light scattering measurements of casein concentration arc made by photodetector 162 at a scattering angle of 140°, as described above. The detector signals are supplied to a process controller 220, which may comprise a personal computer (PC) or other computer or dedicated process controller. The process controller 220 analyzes the measured fat and casein concentrations and generates a control signal based on the fat and casein concentrations. In one example, the control signal varies the fat concentration in the dairy product passing through conduit 200 to achieve a desired casein to fat ratio. It will be understood that different control functions may be based on the measured fat and casein concentrations.

A measurement system for determining fat and casein concentrations in a dairy product is described above in connection with FIGS. 2, 4, 5A, 6 and 7. However, a system of the type described above may be utilized more generally for measuring particle concentrations in a liquid containing relatively large particles and relatively small particles.

Figure 8:
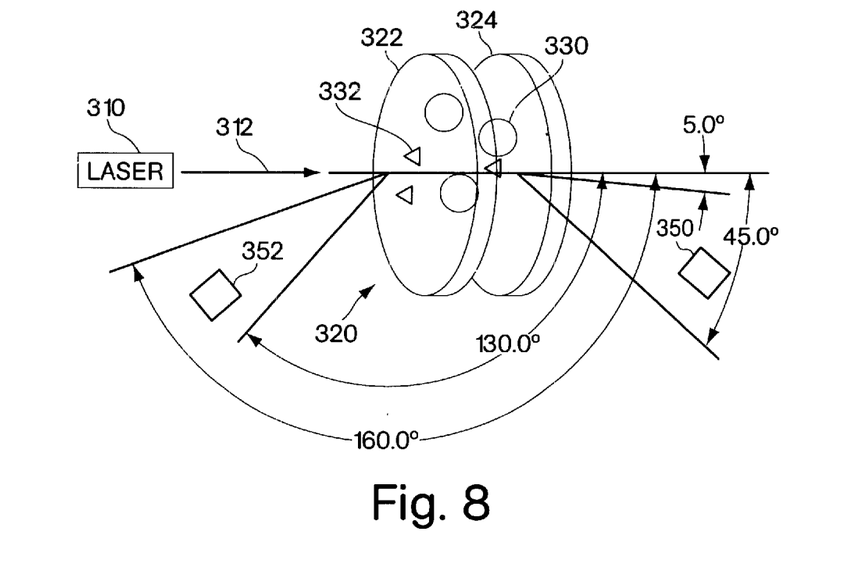
FIG. 8 is a top schematic view of a system for measuring component concentration in a liquid containing relatively large particles and relatively small particles.

A schematic top view of a measurement system in accordance with an embodiment of the invention is shown in FIG. 8. A light source 310 directs a polarized light beam 312 through a scattering cell 320. The light source 310 may be a laser or any other light source that produces a collimated beam. If necessary, the light source includes a polarizing device, such as a polarizing filter, to generate polarized light beam 312. Scattering cell 320 is defined by a first window 322 and a second window 324. A housing (not shown) encloses a cell volume between windows 322 and 324. At least the exterior surface of second window 324 is oriented at or near Brewster's angle with respect to light beam 312, as described above. Scattering cell 320 contains a liquid sample, including relatively large particles 330 and relatively small particles 332.

A first photodetector 350 at an angle of less than 90° with respect to light beam 312 detects scattered light from large particles 330, and a second photodetector 352 at an angle greater than 90° detects scattered light from small particles 332. As described above, photodetectors 350 and 352 do not provide complete separation between fat scattering measurements and casein scattering measurements. Photodetectors 350 and 352 are located in a horizontal plane that passes through light beam 312, where light beam 312 has a vertical direction of polarization. As indicated above, the orientation of the entire measurement system may be varied within the scope of the invention. The range of scattering angles available for measurement is limited because the scattered light must pass either through the first window 322 for large scattering angles or the second window 324 for small scattering angles. The accessible scattering angle ranges are typically 5° to 45° in the forward direction and 130° to 160° in the backward direction, as measured in the laboratory. Thus, detector 350 is positioned within a range of 5° to 45° with respect to light beam 312, and photodetector 352 is positioned within a range of 130° to 160° with respect to light beam 312. Because of refraction effects in windows 322 and 324, the actual scattering angles are 3.44° to 29.92°, corresponding to laboratory angles of 5° to 45°, and 147.03° to 166.33°, corresponding to laboratory angles of 130° to 160°.

In the measurement systems described above, measurements of light scattering from relatively large particles, such as fat particles, and measurements of light scattering from relatively small particles, such as casein particles, may be made simultaneously or at different times. Furthermore, the measurement systems may be configured for measuring one of the particle types. In the measurement system of FIG. 4, photodetector 162 may be utilized for measurements of casein concentration, and photodetector 160 may be omitted if measurement of fat concentration is not required. Alternatively, photodetector 160 may be utilized for measurements of fat concentration, and photodetector 162 may be omitted if measurement of casein concentration is not required. Similarly, in the measurement system of FIG. 8, photodetector 350 or photodetector 352 may be omitted when measurement of the respective particle concentration is not required. In each case, the disclosed measurement system provides the capability to measure particle concentration in a liquid containing both relatively large particles and relatively small particles.

While there have been shown and described what are at present considered the preferred embodiments of the present invention, it will be obvious to those skilled in the art that various changes and modifications may be made therein without departing from the scope of the invention as defined by the appended claims.

What is claimed is:

1. Apparatus for measuring component concentration in a dairy product, comprising:

a light source for generating a polarized light beam having a direction of polarization;

a scattering cell, positioned in the light beam, for receiving a sample of the dairy product, said scattering cell having a first window and a second window, wherein the second window is farther from said light source than the first window, wherein a normal to an exterior surface of the second window is at or near Brewster's angle with respect to the light beam and wherein the direction of polarization of the light beam is parallel to a plane defined by the light beam and the normal to the exterior surface of the second window;

a first light detector, positioned at a first angle in a range of about 5° to about 45° with respect to the light beam, for detecting scattered light from a first component of the dairy product comprising fat having relatively large particle sizes and generating a first detector signal that is representative of concentration of the first component in the sample of the dairy product; and a second light detector, positioned at a second angle in a range of about 130° to about 160° with respect to the light beam, for detecting scattered light from a second component of the dairy product comprising casein having relatively small particle sizes and generating a second detector signal that is representative of concentration of the second component in the sample of the dairy product.

2. Apparatus as defined in claim 1 further comprising a data analyzer, responsive to the first and second detector signals, for generating a signal representative of a casein to fat ratio in the sample of the dairy product.

3. Apparatus as defined in claim 1 wherein said first angle is about 40° and wherein said second angle is about 140°.

4. Apparatus as defined in claim 1 wherein said light source comprises a laser and a polarizing device.

5. Apparatus as defined in claim 4 wherein said light beam has a wavelength in a range of about 780 to 1100 nanometers.

6. Apparatus as defined in claim 1 wherein the first window and the second window of said scattering cell have parallel surfaces.

7. Apparatus as defined in claim 1 wherein said scattering cell includes an inlet port and an outlet port to permit the dairy product to flow through the scattering cell.

8. Apparatus as defined in claim 1 wherein an interior surface of the second window is parallel to the exterior surface of the second window.

9. Apparatus as defined in claim 1 wherein a normal to an interior surface of the second window contacting the sample of the dairy product is at or near Brewster's angle with respect to the light beam, wherein the second window is wedge-shaped.

10. Apparatus as defined in claim 1 wherein said light source comprises a laser diode that generates said polarized light beam.

11. Apparatus as defined in claim 1 further comprising means for diluting the dairy product with water to provide the sample of the dairy product for measurement.

12. A method for measuring component concentration in a dairy product, comprising the steps of:

generating a polarized light beam having a direction of polarization;

placing a sample of the dairy product in a scattering cell that is positioned in the light beam, said scattering cell having a first window and a second window, wherein the light beam is incident on the second window after passing through the sample of the dairy product, wherein a normal to an exterior surface of the second window is at or near Brewster's angle with respect to the light beam and wherein the direction of polarization of the light beam is parallel to a plane defined by the light beam and the normal to the exterior surface of the second window;

detecting scattered light from a first component of the dairy product comprising fat particles, the first component having relatively large particle sizes, at a first angle in a range of about 5° to about 45° with respect to the light beam and generating a first detector signal that is representative of concentration of the first component in the sample of the dairy product; and detecting scattered light from a second component of the dairy product comprising casein particles, the second component having relatively small particle sizes, at a second angle in a range of about 130° to about 160° with respect to the light beam and generating a second detector signal that is representative of concentration of the second component in the sample of the dairy product.

13. A method as defined in claim 12 wherein the step the of detecting scattered light from a first component of the dairy product comprises detecting scattered light from fat particles and wherein the step of detecting scattered light from a second component of the dairy product comprises detecting scattered light from casein particles.

14. A method as defined in claim 12 further comprising the step of generating a signal representative of a casein to fat ratio in the sample of the dairy product in response to the first and second detector signals.

15. A method as defined in claim 12 wherein the step of detecting scattered light at a first angle comprises detecting scattered light at about 40° and wherein the step of detecting scattered light at a second angle comprises detecting scattered light at about 140°.

16. A method as defined in claim 12 further comprises that the step of diluting the dairy product with water to provide the sample of the dairy product.

* * * * *

UNITED STATES PATENT AND TRADEMARK OFFICE
CERTIFICATE OF CORRECTION

PATENT NO. : 6,407,813 B1
DATED : June 18, 2002
INVENTOR(S) : Lovette et al.

It is certified that error appears in the above-identified patent and that said Letters Patent is hereby corrected as shown below:

Column 14,
Lines 5-10, delete claim 13.

Signed and Sealed this

Nineteenth Day of November, 2002

Attest:

JAMES E. ROGAN
Attesting Officer
Director of the United States Patent and Trademark Office